Figure 4:
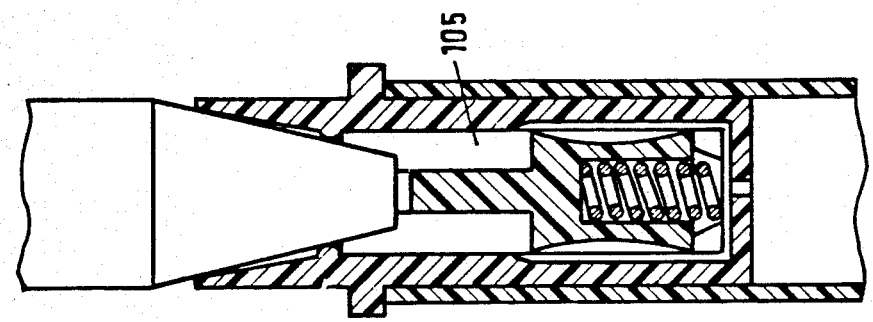

United States Patent [19]

Schwab et al.

[11] Patent Number: 4,710,168
[45] Date of Patent: Dec. 1, 1987

[54] NON-RETURN VALVE FOR MEDICAL PURPOSES IN PARTICULAR FOR BALLOON CATHETERS

[76] Inventors: Egon Schwab, Otto-Schwabe Strasse 4, 6203 Hochheim; Steve Padar, Theresen Strasse 17, 6235 Kelkheim, both of Fed. Rep. of Germany

[21] Appl. No.: 865,907

[22] Filed: May 13, 1986

Related U.S. Application Data

[63] Continuation of Ser. No. 726,071, Apr. 19, 1985.

[51] Int. Cl.$^4$ ............... A61M 25/00; F16K 15/14
[52] U.S. Cl. ............... 604/99; 137/843; 251/149.1
[58] Field of Search ............... 604/96–103; 251/149.1, 149.6, 149.7; 137/843; 141/348, 349

[56] References Cited

U.S. PATENT DOCUMENTS

| | | | |
|---|---|---|---|
| 3,385,301 | 5/1968 | Harautuneian | 604/99 |
| 3,831,629 | 8/1974 | Mackal et al. | 137/843 |
| 3,901,246 | 8/1975 | Wallace | 604/100 |
| 4,429,856 | 2/1984 | Jackson | 137/843 |

*Primary Examiner*—Dalton L. Truluck
*Attorney, Agent, or Firm*—William F. Kilgannon

[57] ABSTRACT

A non-return valve for medical purposes, in particular for balloon catheters, has a hollow valve housing (3) which at one end has a connecting opening (8) for the insertion of a syringe nozzle and two abutments (16, 17) for a slide member (18). The slide member runs with its peripheral surface over at least one valve opening (15) at the cylindrical inside periphery (14) of the housing (3). The first abutment (16) is of such a slightly raised configuration that the slide member (18) can be inserted through the connecting opening (8), by making use of the elastic deformability of the valve housing (3) and/or the slide member. That makes it possible for the second abutment (17), at the end in opposite relationship to the connecting opening (8), to be already ready moulded in the manufacturing process.

10 Claims, 4 Drawing Figures

NON-RETURN VALVE FOR MEDICAL PURPOSES IN PARTICULAR FOR BALLOON CATHETERS

This is a continuation of co-pending application Ser. No. 726,071, filed on Apr. 19, 1985.

The invention relates to a non-return valve for medical purposes, in particular for balloon catheters, wherein a hollow valve housing is provided at one end with a connecting opening for the insertion of a syringe mouthpiece, at the other end has at least one through opening and in its interior, adjacent the connecting opening, has a first abutment and, displaced towards the oppositely disposed end, has a second abutment for a closure portion, and the closure portion can be displaced by the syringe mouthpiece against an elastic force from a closed position of closing off the end openings relative to each other into an open position of interconnecting said openings.

In a known non-return valve of that kind (U.S. Pat. No. 3,831,629), the first abutment serves as a valve seat against which a shoulder of the closure portion bears in the closed position. For the purposes of guidance in the space inside the valve housing, the closure portion is provided with axial ribs on its outside. The rearward end of the closure portion bears against the second abutment and can be elastically deformed in the axial direction. The second abutment is formed, after the closure portion has been fitted into the interior of the valve housing, by a cylindrical edge portion which is formed integrally with the housing being subsequently flanged over in an inward direction.

The flanging operation represents an additional working step which makes manufacture more difficult. It also constitutes a considerable restriction on the number of plastic materials that can be used for making the valve housing. Furthermore, difficulties are incurred in effecting the flanging-over operation in such a way that, in the rest condition, the closure portion is pressed against the seat by a predetermined axial pressure.

The invention is based on the object of providing a non-return valve of the kind set forth in the opening part of this specification, the production of which does not require any additional working operation for forming the second abutment.

According to the invention, that object is attained in that the second abutment is formed on the valve housing, that the closure portion is a slide member which with its peripheral surface controllingly runs over at least one valve opening at the cylindrical inside periphery of the valve housing, and that the first abutment is of such a slightly raised configuration that the slide member can be introduced through the connecting opening, by making use of the elastic deformability of the valve housing and/or the slide member.

Because of the design configuration in the form of a slide valve, the first abutment is no longer required as a valve seat. It only has to prevent the closure portion from falling out, and comparatively small surfaces on the first abutment are sufficient for that purpose. Consequently, the first abutment can be formed with such a slightly raised configuration that, upon assembly, the closure portion can be moved into position with only a slightly increased force applied thereto. Therefore, in the operation of injection moulding the valve housing, the second abutment can be moulded in its definitive configuration as the operation of introducing the closure portion is effected from the end of the first abutment and not from the end with the second abutment. Another advantage of the valve is that the sealing force does not depend on axial elastic forces but is governed by the dimensions of the valve housing and the closure portion at the inside and outside peripheries respectively. In addition, without any additional measures, a slide member is also properly guided in the housing, particularly if it is of an appropriate length.

It is advantageous for the second abutment to be carried by a stiff end wall which is formed integrally and jointly with the valve housing. In that way, the valve housing is strengthened at the end that is opposite to the first abutment. It can therefore be of a comparatively thin-walled configuration, which facilitates elastic expansion when the closure portion is introduced.

In particular, the first abutment may be an annular bead. When using an annular bead, a very shallow raised configuration is sufficient to still provide an adequate abutment surface.

It is of particular advantage for the slide member to have at least two peripheral sealing lips which are displaced in the axial direction relative to each other. Such a slide member may be assembled in a very simple fashion as the sealing lips can be more easily pushed over the first abutment, than a continuous cylindrical surface.

It is also desirable for the slide member, at least over a part of the axial length thereof, to have a cavity which communicates with the through opening. If the non-return valve is to seal off a pressure, that pressure also acts in the cavity in the slide member and assists the radially outwardly acting sealing forces.

For the purposes of producing the elastic force, in particular a coil spring which is supported in the region of the second abutment against the valve housing may engage the slide member. The coil spring may be of such a size that it returns the slide member into its rest position against the first abutment when it is no longer loaded by the syringe mouthpiece or nozzle.

In particular, the coil spring may extend into the cavity in the slide member. The spring can therefore be comparatively long so that the spring force experiences comparatively little change during the stroke movement of the slide member.

A preferred embodiment provides that the at least one valve opening passes through the peripheral wall of the valve housing and is connected to a groove at the outside periphery of the valve housing, the groove being covered from the outside and also forming the through opening. Such a valve housing can be easily shaped or moulded. In the simplest case, the external groove is covered over by the end of the hose or tube which is pushed on over the valve housing.

In another embodiment, the at least one valve opening is formed by a groove at the inside periphery of the valve housing, which is of greater axial extent that the sealing length of the slide member. As the flow passages extend only in the interior of the housing, that arrangement ensures that trouble does not occur in an external passage in the housing, in the event of the hose being excessively stretched or due to the adhesive connection not being entirely satisfactory.

Desirably, the at least one valve opening is at a greater axial spacing from the first abutment, than the sealing length of the slide member. In that case, in the closed position, the entire sealing length is between the connecting opening and the valve opening, thus giving a particularly good sealing action.

The slide member can be made of very small diameter. The diameter of the valve housing is then also of a correspondingly small size. In particular, the outside periphery of the valve housing should be cylindrical and 7 mm in diameter. Such a non-return valve can be used without an additional adapter for the most widely employed tube sizes, namely for a rubber tube with an inside diameter of about 6.0 mm and for a plastic tube with an inside diameter of about 7.2 mm. The valve housing fits into the rubber tube with a tight expansion fit. On the other hand, it fits into a plastic tube with a small amount of clearance, and can be secured to the plastic tube by adhesive or secured in position by means of a collar.

Figure 3:
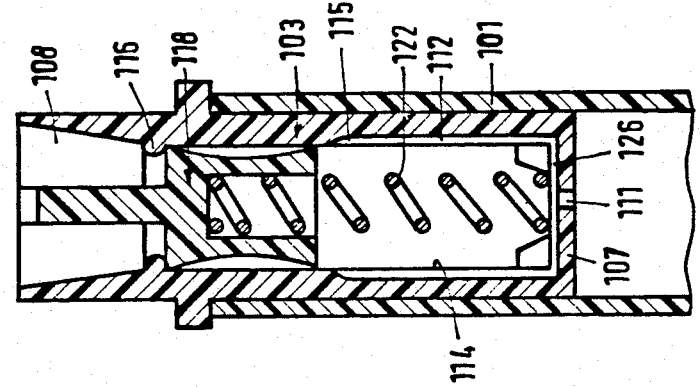
Figure 2:
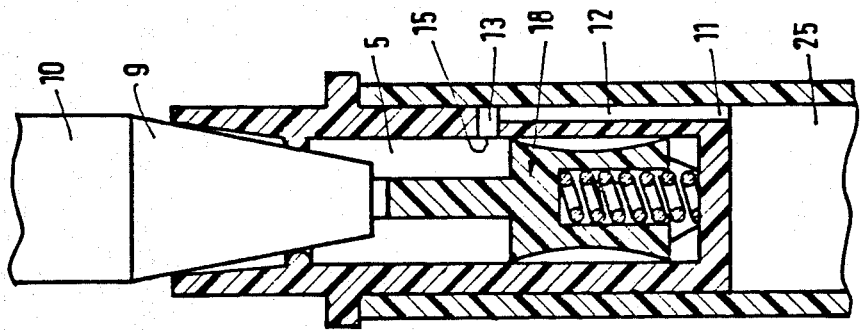
Figure 1:
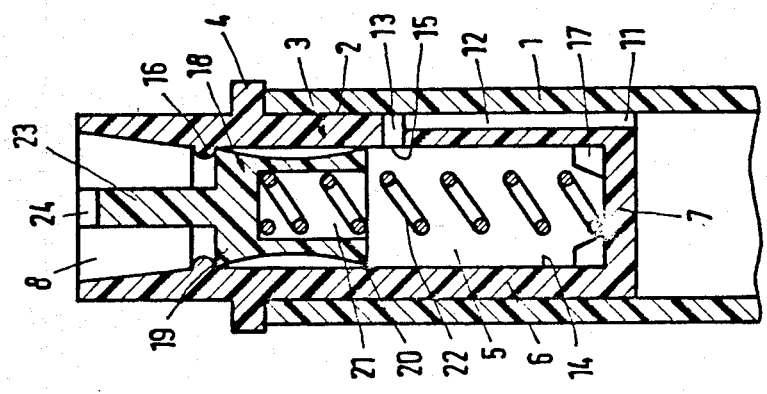

The invention will be described in greater detail hereinafter with reference to preferred embodiments which are illustrated in the drawing in which:

FIG. 1 is a view in longitudinal section through a non-return valve according to the invention, in the closed position, FIG. 2 shows the non-return valve of FIG. 1 in the open position, FIG. 3 shows another embodiment in the closed position, and FIG. 4 shows the FIG. 3 embodiment in the open position.

In the embodiment shown in FIGS. 1 and 2, the end of a hose or tube 1 which leads for example to an inflatable balloon of a catheter is pushed onto the outside periphery 2 of a valve housing 3 until it butts against a flange 4. The tube 1 can be held at the position by inherent elasticity, for example if it comprises rubber or another elastic material, but it can also be secured in position by adhesive means or retained in place by an additional clip, collar or the like. The valve housing 3 has a space 5 in its interior, which is surrounded by a peripheral wall portion 6 and which is closed off by a rigid end wall portion 7 which is formed integrally with the peripheral wall portion 6. At one end, the valve housing 3 has a conical connecting opening 8 for insertion of the conical nozzle or mouthpiece 9 of a spray or syringe 10 while at the oppositely disposed end there is a through opening 11 which is formed by the end of an axial external groove 12 in the peripheral wall portion 6. The groove 12 communicates with the space 5 inside the valve housing 3 by way of a radial bore 13, a valve opening 15 being formed at the inside periphery 14. Disposed adjacent the connecting opening 8 is an inwardly directed first abutment 16 in the form of a shallow annular bead. A second abutment 17 projects upwardly from the end wall portion 7, in the form of individual blocks which are displaced in the peripheral direction.

A slide member 18 which forms the closure member of the non-return valve is displaceable between the two abutments 16 and 17. The slide member 18 has two peripherally extending sealing lips 19 and 20 which, under the influence of radial forces which are predetermined by the dimensions of the slide member 18, with respect to the valve housing 3, bear sealingly against the inside periphery 14 of the valve housing 3. The slide member 18 has a cavity 21. A coil spring 22 engages into the cavity 21, the coil spring being supported between the blocks of the second abutment 17 on the end wall portion 7 and urging the slide member 18 into the closed position shown in FIG. 1. For the purposes of mechanically coupling it to the mouthpiece 9, the slide member 18 has an outwardly projecting pin portion 23 with a transverse groove 24 in its end. As shown in FIG. 2, the mouthpiece 9 can engage the pin portion 23 and urge the entire slide member 18 towards the second abutment 17, compressing the spring 22, whereby the non-return valve moves into its open position.

In the open position of the valve, air or another fluid which is supplied by the syringe 10 flows into the upper part of the space 5 and by way of the valve opening 15, the radial bore 13, the external groove 12 and the through opening 11, into the interior 25 of the tube 1 and thus to the location at which it is to be used or consumed.

When the mouthpiece 9 is withdrawn, the slide member 18 returns into the closed position shown in FIG. 1, under the force of the spring 22. In the closed position, both sealing lips 19 and 20 lie between the connecting opening 8 and the valve opening 15 so that the interior 25 of the tube is securely sealed off with respect to the connecting opening 8. In that respect, the pressure in the tube 1 acts in addition to the spring 22 to hold the slide member 18 in the closed position shown. Therefore, the spring 22 only needs to have a slight biasing force in the extended position shown in FIG. 1. The spring can therefore be made comparatively weak and inexpensively.

The pressure also acts in the cavity 21. The higher the pressure, the greater are the radial forces which act at least on the sealing lip 20 so as to ensure the sealing action.

The slide member 18 and the valve housing 3 are injection moulded from plastic material and then automatically assembled. For that purpose, the spring 22 and the slide member 18 only have to be pushed into the space 5 inside the valve housing. In that operation, the slide member 18 can be pushed past the first abutment 16 because that abutment is raised in an inward direction above the inside periphery 14 to such a slight degree that the usual elasticity of the plastic materials of the valve housing 3 and/or the slide member 18 is sufficient to produce the deformation required for that purpose. The plastic materials are not subject to high requirements. Therefore, it is possible to carry out a high-speed injection moulding manufacturing operation, thus giving very low cost levels. The plastic material used may be for example a polyolefin or the like. Manufacture is therefore simple and inexpensive. The non-return valve can therefore be supplied as a cheap throw-away article.

In the embodiment illustrated in FIGS. 3 and 4, the same reference numerals are used to denote corresponding parts, but increased by 100. Essentially the differences are that axial grooves 112 which are formed on the inside periphery 114 are provided as the valve opening 115, which grooves 112 can also be extended in the form of grooves 126 in the end of the arrangement. The through opening 111 is disposed at the centre of the end wall portion 107.

When in this case the slide member 118 is displaced from the closed position shown in FIG. 3 into the open position shown in FIG. 4, the air or the fluid flows only in the space 105 inside the valve housing 103. The axial grooves 112 cannot become obstructed from the outside.

The non-return valve may be used for a very wide range of medical purposes which involve seeking to achieve a sound and reliable closure of a space which is under an elevated pressure and which is to be filled by means of a syringe. In particular, the above-mentioned space may be a balloon which is disposed at the front end of a catheter tube and which is connected to the non-return valve by way of a passage additional to the catheter tube and which serves for fixing the catheter tube in position after it has been introduced into the human body. For the purposes of emptying the above-indicated space, the slide member 18 only needs to be moved with the mouthpiece 9 into the open position, whereupon the air or the fluid escapes or can be sucked away with the syringe.

We claim:

1. In a non-return valve suitable for medical purposes comprising a hollow valve housing having an opening to receive the mouthpiece of a syringe, said housing having a first abutment at its syringe-receiving end and a second abutment at its opposite end to thereby contain a valve closure member; a reciprocal, valve closure member disposed within the valve housing and displaceable by a syringe, the improvement which comprises a valve housing having a first slight abutment disposed inwardly of the interior wall of the housing so as to facilitate entry disposing of the valve closure member within the housing, a slidable valve-closure member having a peripheral surface in constant contact with the interior wall of the valve housing when the valve is in open or closed position; and an opening in the interior wall of the valve housing which communicates with an opening in the syringe mouthpiece through axial displacement of the valve closure member past the opening in the interior wall of the housing.

2. A non-return valve as set forth in claim 1 and further wherein a second abutment is carried by a rigid end wall formed integrally with the valve housing.

3. A non-return valve as set forth in claim 2 and further wherein the first abutment is an annular bead.

4. A non-return valve as set forth in claim 1 and further wherein the valve closure member has at least two peripheral sealing lips which are displaced relative to each other in the axial direction.

5. A non-return valve as set forth in claim 4 and further wherein the valve closure member, at least over a portion of its axial length, has a hollow space which communicates with the opening in the interior wall of the valve housing when the valve is in the end position.

6. A non-return valve as set forth in claim 5 and further wherein a coil spring which bears against the valve housing in the region of the second abutment engages the valve-closure member.

7. A non-return valve as set forth in claim 6 and further wherein the coil spring extends into the hollow space in the valve closure member.

8. A non-return valve as set forth in claim 1, wherein at least one opening in the interior wall of the valve housing passes through the wall of the housing and communicates with a closed groove formed at least in part by the outer wall of the valve housing, said groove extending along the longitudinal axis of the housing from the interior wall opening to the end of the housing distal to the syringe receiving end.

9. A non-return valve as set forth in claim 1, and further wherein at least one opening in the interior wall of the housing is formed by a groove at the inside wall of the valve housing, which groove is of greater axial extent than the sealing length of the valve closure member.

10. A non-return valve as set forth in claim 1, and further wherein at least one opening in the interior wall of the valve housing is at a greater axial spacing from the first abutment than the sealing length of the valve closure member.

* * * * *